United States Patent [19]

McDowell

[11] Patent Number: 4,909,609
[45] Date of Patent: Mar. 20, 1990

[54] NONLINEAR OPTICAL PROTECTION AGAINST FREQUENCY AGILE LASERS

[75] Inventor: Vaughn P. McDowell, Fredericksburg, Va.

[73] Assignee: The United States of America as represented by the Secretary of the Navy, Washington, D.C.

[21] Appl. No.: 228,215

[22] Filed: Aug. 4, 1988

[51] Int. Cl.⁴ .............................................. G02F 1/01
[52] U.S. Cl. ................................. 350/354; 350/96.27; 350/96.32; 350/330
[58] Field of Search ............... 350/96.29, 96.32, 96.34, 350/96.27, 354, 334, 331 R, 330

[56] References Cited

U.S. PATENT DOCUMENTS 3,620,597 11/1971 Schwartz et al. .................. 350/354
4,176,919 12/1979 Rast, Jr. ............................ 350/354
4,515,429 5/1985 Smith et al. ..................... 350/354 X
4,776,677 10/1988 Park et al. ......................... 350/354

Primary Examiner—Eugene R. Laroche
Assistant Examiner—Nathan W. McCutcheon
Attorney, Agent, or Firm—John D. Lewis; Kenneth E. Walden

[57] ABSTRACT

An eye protection or equipment filter device for protection from laser energy is disclosed. The device may be in the form of a telescope, binoculars, goggles, or constructed as part of equipment such as image intensifiers or range designators. Optical elements focus the waist of the beam within a nonlinear frequency-doubling crystal or nonlinear optical element or fiber. The nonlinear elements produce a harmonic outside the visible spectrum in the case of crystals, or absorb the laser energy in the case of nonlinear fibers. Embodiments include protectors for the human eye as well as filters for sensitive machinery such as TV cameras, FLIR systems or other imaging equipment.

5 Claims, 3 Drawing Sheets

NONLINEAR OPTICAL PROTECTION AGAINST FREQUENCY AGILE LASERS

The invention described herein was made by an employee of the U.S. Government and may be manufactured and used by or for the Government for governmental purposes without the payment of any royalties thereon or therefor.

This invention concerns a method and devices for protecting the human eye and light sensitive equipment from laser energy. More specifically, a protection method is disclosed that does not interrupt the normal light energy to the equipment or the eyes of the receiver.

BACKGROUND OF THE INVENTION

Many military systems rely on sensitive optical detectors for gathering information. Forward-looking infrared radars (FLIR), night-vision goggles, and the human eye (perhaps aided by a telescope or binoculars) are all examples. Image intensifiers of the old cascade tubes are giving way to microchannel plates providing a new range of ultrasensitive intensifiers. For example, in Jervis, M. H., and Needham, M. J., *Image Intensifiers and Infrared Detectors,* British Electro Optics, edited by Baker, L. R., published by Taylor & Francis, Ltd., London, 1977, at 31, several new highly sensitive devices are disclosed.

Along with this newly developing technology are newly developing problems. One such problem is that these systems suffer damage from bright sources that operate in the detector's band. One such bright source is a hostile laser. Protection against these countermeasure weapons have been rudimentary and either use a filter network to exclude the band of wavelengths containing the bright source or employ a shutter to close off input when it contains a high intensity component. A very fast shutter is needed. Such a shutter should be capable of sensing a threat and closing in nanoseconds because that is the potential rise time of an optical threat.

Problems remain with both a filter and shutter method of protection. One problem is that the filter excludes a band of the spectrum being received and the shutter closes the input signal completely off. Another problem is the new, agile laser weapon which covers an entire spectrum of frequencies. No protection exixts in the art today that can protect from changing frequency hostile lasers and still provide an optical input to the receiver.

The optimum protection circuit should discriminate and protect against dangerously intense sources without closing the input field, should react to any and all frequencies of high intensity energy and must have a response time that intercepts the high intensity source during its rise time before damage to the eye or sensitive equipment can occur.

OBJECTS OF THE INVENTION

It is therefore an object of the present invention to provide an eye protection device against hostile laser radiation.

It is another object of the instant invention to provide a protection device against changing frequency laser energy.

It is still another object of this disclosure to teach a method of protection against laser energy that does not block normal vision.

Yet another object of the present invention is to teach a system that is completely passive without the requirement of batteries or power supply.

It is a further object of this invention to teach a means of eye protection that allows the user to view the scene in color while being illuminated with hostile laser energy.

It is yet another object of the instant invention to disclose a protection device that is effective against high speed pulsed lasers, e.g., pulsed frequency doubled Nd:YAG green light antipersonnel weapons.

It is still another object to teach a method of eye protection against all frequency laser energy, that can be incorporated into a telescope or binoculars.

It is a further objective to disclose a device for protection against laser energy that is compatible with microchannel image intensifiers.

It is another object of the instant disclosure to teach a device for protecting the eyes of field military personnel using launcher sights, range finders, range designators or other military equipment requiring a visual field.

A further object is to disclose a method that can provide protection from a hostile laser source and still allow the receiver to record the position and existence of the high energy source.

Another object of the invention is to provide protection for the eye to any wavelength, hence to frequency agile lasers or lasers of any color.

SUMMARY OF THE INVENTION

According to the present invention, the foregoing and additional objects are attained by providing a nonlinear crystal or material within the input path of the equipment or viewing device where the normal intensity spectrum passes unimpeded, but any high intensity source is either absorbed or changed into a harmonic outside of the desired spectrum and filtered. The invention may use more than one filter and is adaptable with lenses to construct a telescope or binoculars. A preferred embodiment uses fiberlike tubes containing a nonlinear optical fluid that absorbs high intensity laser energy while passing the low intensity spectrum. This device may employ an array of these optic fibers which facilitates matching with the new fiber array image intensifiers. The system is passive in all respects.

The operation of nonlinear optic material in generating harmonics from the fundamental incoming laser frequency is known to those skilled in the art. For a more detailed mathematical description, the interested reader can turn to a textbook such as Harvey, A. F. *Coherent Light,* Wiley-Interscience, New York, 1970, at 929–931.

Nonlinear optic material is also known to exhibit certain losses resulting in absorption of the fundamental laser frequency. A standard textbook, Yariv, A., *Introduction to Optical Electronics,* Holt, Rinehart, and Winston, Inc., New York, 1971, at 186–188. A. Yariv mathematically described both the generation of harmonics and fundamental laser energy absorption.

BRIEF DESCRIPTION OF THE DRAWINGS

A more complete appreciation of the present invention and many of the attendant advantages thereof will be readily apparent as the same becomes better understood when considered in connection with the accompanying drawings wherein.

DETAILED DESCRIPTION OF THE INVENTION

Figure 1:
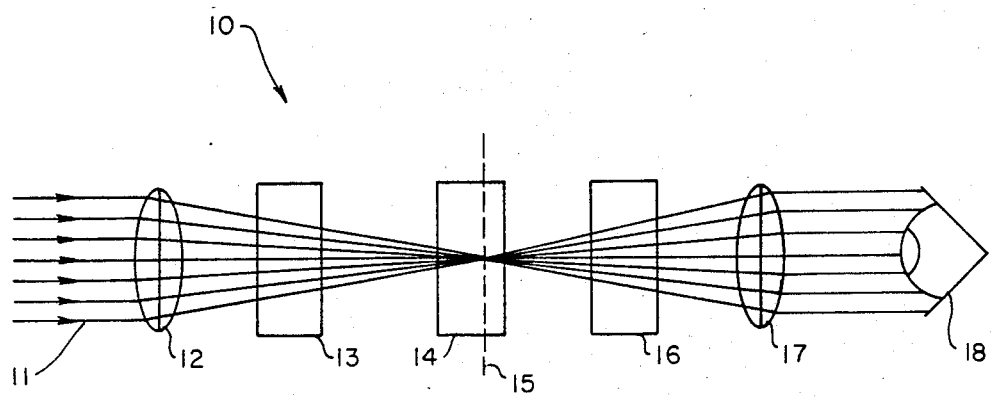
FIG. 1 is an optical schematic of a telescope containing the protection device with some common optical elements left out for simplicity.

Turning now to FIG. 1, the numeral 10 designates generally one embodiment of an optical device containing the protection method of the present invention. The light energy 11 enters a common input object lens 12 such as that used in a telescope where it is focused through a filter 13 to a focal point within a frequency doubling crystal 14 at a point where an image plane 15 is formed within the crystal. From the image plane 15 the light energy is passed through a second filter 16 to an eyepiece lens and into the receiver 18 that in the embodiment illustrated in FIG. 1 is a human eye. Other standard optical elements may be employed; for example, an optical polarizer might be included in the path of light energy 11 located between the first filter 13 and the frequency doubling crystal 14. This standard optical element was not included in the embodiment of FIG. 1 for simplicity. A person skilled in the art will quickly recognize that FIG. 1 represents a simple telescope with the addition of the filters 13 and 16, and the frequency doubling crystal 14. Should the receiver require it, an additional optical element can be included to invert the image, for the simple device illustrated in FIG. 1 yields an inverted image.

The objective lens 12 is a standard optical element that concentrates the incident light rays 11 to a high intensity at the focal point 15. A high intensity is required in order for the frequency doubling crystal 14 to efficiently generate the 2nd harmonic. The greater the intensity of the incident light the greater the efficiency of the 2nd harmonic generation within crystal 14.

The first filter designated 13 in FIG. 1 allows only the desired portion of the optical spectrum to enter crystal 14. The filter will be chosen to correspond with the sensor that one desires to protect. In the case of the human eye, as illustrated in FIG. 1, it is desired that the entire visible spectrum pass through the system. The visible spectrum, from deep red, circa 7000 Å, to 4000 Å, violet, should pass through filter 13 unimpeded while anything having a wavelength greater than 7000 Å that is in the infrared portion would be filtered. Likewise, the ultraviolet spectrum with wavelength shorter than 4000 Å would be filtered by the first filter 13. It is important to note that any lasers operating in the infrared and ultraviolet bands will be filtered by filter 13 while any laser energy in the visible spectrum will enter the frequency-doubling crystal 14. Various filters are available from multiple commercial sources, and those used in the development described herein were purchased from Kodak.

Crystal 14 is mounted in a position such that the incident rays are focused inside of the crystal. Lenses suffer from aberrations, i.e., chromatic, coma, curvature, etc., thus, if crystal 14 is sufficiently thick a focus will occur within the crystal's boundaries, shown at line 15 in FIG. 1. The crystal converts the incident, coherent, high-intensity component of input 11 into ultraviolet light while remaining transparent to low level visible radiation. For example, if a ruby laser with a wavelength of 6943 angstroms is incident on the system, crystal 14 will convert the energy to its second harmonic having a 3472 angstrom wavelength in the ultraviolet spectrum. A wavelength without the visible light spectrum. Likewise, a tunable dye laser operating at a 5000 Å wavelength would be converted to a second harmonic of 2500 Å in crystal 14, again out of the visible spectrum. In fact, any laser operating in the visible spectrum will be doubled in crystal 14 and produce a second harmonic out of the visible spectrum.

Second filter 16, used when the human eye is the sensor to be protected, absorbs ultraviolet and passes or is transparent to the visible portion of the spectrum. What passes on to eyepiece 17 is only low level visible radiation at an intensity below the damage threshold to the human eye or other receiver. The harmonics, both the 2nd and any other harmonic generated in the frequency doubling crystal, will be filtered.

Note that the objective lens 12 focuses an image in a focal plane located in the 2nd harmonic crystal. The eyepiece transfers that image to the eye or other sensor 18. The received image in FIG. 1 is inverted. Other optical elements to invert or otherwise process the received image may be incorporated within the scope of this invention; although, for simplicity, additional elements have not been illustrated in FIG. 1.

The heart of the device illustrated in FIG. 1 is a frequency doubling or 2nd harmonic crystal 14 that has a property of generating the 2nd harmonic of high intensity coherent light. Furthermore, these frequency doubling crystals have a transparent property to low level visible light, thus passing an image of the field onto the sensor while doubling any high power coherent light which is then filtered. It is interesting to note that the 2nd harmonic generated by crystal 14 is lower in magnitude as well as doubled in frequency.

Frequency doubling was first observed in 1961 by Franken and coworkers when they focused a pulsed ruby laser onto a quartz crystal. This first experiment resulted in conversion efficiencies of 1 percent. Since then crystals producing much greater efficiencies have been noted. It is considered within this invention to use whatever crystal provides the best response and efficiency for the receiver. Some crystals known to frequency double and having good efficiencies are ADP, KDP and sodium nibate. These and many other possible crystals are readily available on the commercial markets, and known to those skilled in nonlinear optics.

Because frequency doubling and filtering are not 100 percent sufficient, a sentry viewing the field with a telescope containing the nonlinear optical protection would see a twinkling of energy from the laser source telling him a hostile laser was irradiating him without endangering his eyes or interrupting his surveillance. His protection remains independent of the frequency of the hostile laser and will protect him from fixed frequency and agile moded sources alike.

Another advantage to the frequency doubling crystals are their small size and weight allowing embodiment of the optical protection system to be incorporated in the night vision goggles or binoculars as well as telescopes.

While crystals are the simplest nonlinear optical frequency-doubling devices and therefore chosen for embodiment in FIG. 1, other optical elements exhibit nonlinear properties and may be used to construct the optical protection disclosed herein.

One such embodiment users an array of non-linear microchannels or microfibers which absorb laser light. This nonlinear optic material, formed in clusters of microchannels, is chosen to have a very high absorption coefficient to nonlinear energy. An array of microfibers also conveniently facilitates use with a microchannel image intensifier as no eyepiece is required. In this adaptation the microchannels of nonlinear material connect directly to the microchannel input of the image intensifier.

The nonlinear optic material will be a design choice determined by the nature of the expected laser energy and the type receiver to be protected. The optic material may be a liquid or a solid. One example of one class of solid, nonlinear, optic material is polydiacetylenes. These and other polymers, with molecular engineering, are adaptable over a wide range for use in optical protection devices. The optical parameters of several of these type materials are discussed in Shard, M. C. and Chance, R. R. *"Nonlinear Optical Properties of Polydiacetylenes,"* American Chemical Society Symposium, Series 233, Kansas City, Mo., September 1982, pp. 187-212.

Liquid crystals are a second class of materials available to perform as nonlinear optic material in protection devices. Several liquid crystal mediums are evaluated in Khoo, I. C. and Shen, Y. R., *"Liquid Crystals: Nonlinear Optical Properties and Processes."* Optical Engineering, Vol. 24, No. 4, July/August 1985, p. 579. The exact material is in many respects a designer material that one skilled in the art of nonlinear optics will prepare using molecular engineering to match the parameters needed in each application. The organic polymers produce excellent and controllable nonlinear optic material.

Because an array of nonlinear fibers or microchannels both convert laser energy to harmonic energy as well as absorb the harmonic energy, they do not require a filter. The frequency doubling crystals must also have a filter to absorb the harmonic, the microfiber/microchannel array is the preferred embodiment. It is to be within the scope of this invention to use a filter with the array should extra protection be desired, however.

Figure 2:
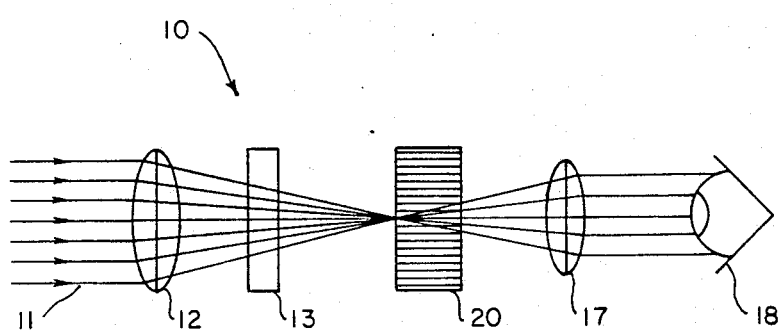
FIG. 2 is an optical schematic of a telescope containing a specie of the protection device utilizing a multifiber/multichannel nonlinear array.

Turning now to FIG. 2, a direct view optical system for protection against laser energy using a microchannel array of nonlinear fibers is disclosed. Again, a human eye 18 is depicted as the receiver for simplicity, but the invention may be practiced with all optical viewing and sensing equipment.

Again, for simplicity, the object lens 12 and eyepiece 17 are standard lenses and constitute a telescope with an inverted output. The filter 13 and microchannel fiber array 20 are the active elements which provide the protection. The filter 13 transmits only the visible portion of the spectrum and blocks the infrared and ultraviolet spectrum. The visible scene, e.g., advancing troops, ships, etc., as well as any visible laser energy, is unaffected by filter 13 and continues on its focal path to focus upon the microfiber/microchannel (MF/MC) device. This nonlinear device MF/MC 20 possesses two properties. It converts the intense laser light into ultraviolet energy and then the material absorbs the ultraviolet energy. It should be noted that some receivers input ultraviolet or infrared and in these cases the filter would, of course, pass the wanted part of the spectrum and block the rest.

The objective lens 12 also focuses nonlaser radiation that is the normal visible spectrum on the face of the MF/MC array 20. Because this light is noncoherent and of normal intensity, the MF/MC array 20 transmits it straight through without absorbing the energy. The fibers are small enough to obtain resolution greater than 30 line pairs per millimeter. The more line pairs, the greater the resolution. This array, constituting this large number of fiber channels transmits the image focused by the objective lens.

Figure 3:
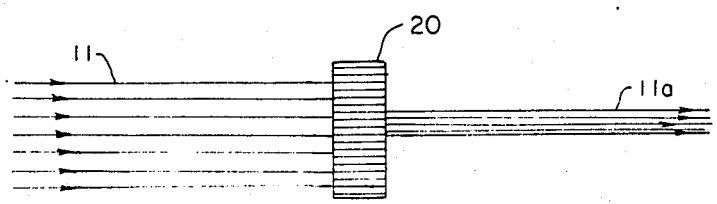
FIG. 3 is a pictorial representation of the change in optical energy resulting from the protective device of FIG. 2.

FIG. 3 depicts the amplitude of the spectrum as it passes through MF/MC array 20. The high laser energy 11 enters MF/MC array at one high amplitude and exits at a much lower level 11a. In this sense it truncates the high intensity laser energy.

One of the critical requirements for producing nonlinear effects is the intensity of the incoming laser radiation. The greater the intensity, the greater the efficiency. The MF/MC array 20 therefore should be operatively spaced from objective lens 12 so as to place it within the focal plane. This increases efficiency. Using materials having high nonlinear coefficients allows the system to function within a range of high and low intensity inputs. The protection is available to continuous wave (CW) lasers such as copper, argon, etc., as well as frequency-doubled high peak-power Q-switched (green light) lasers such as the Nd:YAG.

The visible scene can be viewed even while the operator is being illuminated by a hostile laser weapon. When the MF/MC array is doubling and absorbing the intense laser energy, the visible scene continues to pass unaffected. There is no shutter action except within the tiny area where the laser light source is narrowly focused on the MF/MC array.

Figure 4:
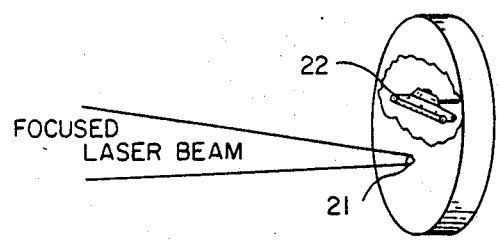
FIG. 4 is a pictorial of the shape and optical pattern of a disk-shaped multifiber/multichannel nonlinear array.

This effect can be graphically viewed in FIG. 4 where a circular MF/MC array 20 is shown with a focused visible light source impinging on a few pixels at point 21 while 22, illustrated as a tank and representing the visual scene, is passed through MF/MC array 20. Only the channels or pixels at the small spot 21 act as shutters or absorbers and impede the optical energy passing through the device.

Microfiber/microchannels are widely known in the art of image intensifiers, and the nonlinear material can be a solid or a liquid. They are essentially an optical fiber. If a solid is used it is formed into a fiber. It a liquid is used, when the liquid is contained in a tube or channel. The spacing of these fibers or tubes are to be greater than 30 line pairs per mm. for good resolutions.

Figure 5:
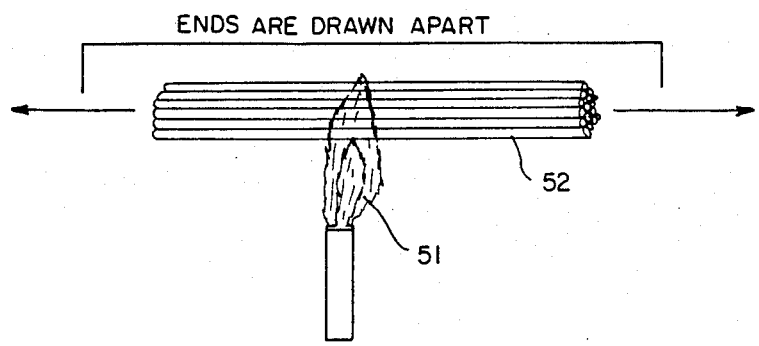
FIG. 5 is an artist's conception of the first step in manufacturing multichannel nonlinear fluid optics used to construct one type of the nonlinear array of FIG. 4.
Figure 5A:
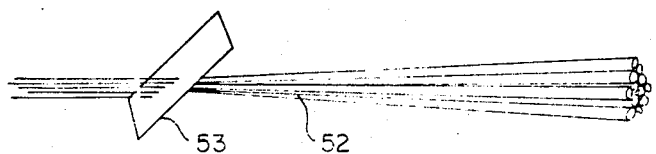
FIG. 5a is an artist conception of another step in the manufacturing process of FIG. 5.

FIGS. 5 and 5a show one technique for forming the microfiber array using a nonlinear optical fluid. In FIG. 5 a flame or heat source 51 heats a bundle of glass tubes 52 which are then drawn. FIG. 5 to the desired diameter and length and then cut with a cutting device 53. The individual sections are then assembled in an array and the ends of the tubes then polished. The ends of the microchannel are then fitted with glass plates, filled with fluid and sealed.

If solid fibers are chosen for use, the fibers are simply bundled into an array, cut and formed into a MF/MC disk or element. Optical couplers used in image intensifiers use similar technology and both techniques are known in the art. The finished MF/MC disk in FIG. 4 illustrates the general shape of the array when it is cut and polished in a disk shape.

The operation of a nonlinear optical device inputs a discrete frequency laser source which is focused to be incident within the nonlinear crystal or on the MF/MC array. The output is twice the frequency of the input and is the second harmonic. Other harmonics may be generated but are generally low enough in power to be disreguarded, but if not the nonlinear material will absorb these also.

This second harmonic wave is not instantaneously generated, but builds up gradually as the wave travels through the length of the nonlinear material. Because the second harmonic builds to a peak, it is necessary to size the nonlinear element to maximize efficiency. The highest peak of the second harmonic occurs when the output second harmonic is phase matched with the input. As a phase mismatch develops the efficiency of the nonlinear element decreases. The efficiency is expressed as the ratio of power-out to power-in and is a function of phase matching.

Typically phase mismatching in the nonlinear material is due to the fact that the wave velocity of the fundamental and second harmonic differ; that is the index of refraction is wavelength dependent. This is corrected by using birefringent crystals where the velocity of light in this material is dependent on the orientation of the crystal, known as the fast and slow axis. Typically, these crystals are used for generating intense green laser light from infrared lasers such as Nd:YAG. Now to obtain near perfect phase matching, the crystal is oriented such that both waves travel at the same velocity. In this instance, one skilled in the art will recognize that the addition of an optical polarizer between filter 13 and crystal 14 in FIG. 1 will facilitate optical alignment and efficiency.

One of the main limitations in efficient second harmonic wave production (even in perfect phase matching) is that the second harmonic wave tends to walk away from the fundamental wave as the path through the material increases. This is why, even in the perfect phase match condition, that the amplitude reaches saturation. Typical efficiencies are in the order of 40 percent, but as high as 80 percent have been reported.

To provide eye protection, the device must efficiently absorb hostile laser light; that is absorb nonlinear energy. To do this, the nonlinear material converts the laser energy to second harmonic energy which is absorbed as fast as it is produced. Microsize nonlinear fibers or microchannels can satisfy the above.

The power-out to power-in ratio is the measure of second harmonic conversion efficiency. Another factor of equal importance is the degree of absorption. In the MF/MC device, a cyclic production of harmonic energy is produced even if the phase match is not perfect. The nonlinear material provides short path absorption and can absorb each cycle where second harmonic energy is being produced. Each time a cycle is absorbed the hostile laser energy is absorbed. If the length of the microfiber or microchannel is sufficiently long, then all of the hostile energy will be absorbed. The precise length will vary according to the nonlinear coefficients of the optical fluid or fiber chosen along with the degree of phase mismatch.

The mathematical relationships of the fundamental and second harmonic waves can be described with the following equations:

Fundamental $$\frac{dE_1}{dz} = -\frac{\sigma_1}{2}\sqrt{\frac{\mu_0}{\epsilon_1}}E_1 - i\omega_1\sqrt{\frac{\mu_0}{\epsilon_1}}\,dE_3E_1^*e^{-i(\Delta k)z}$$

Second Harmonic $$\frac{dE_3}{dz} = -\frac{\sigma_3}{2}\sqrt{\frac{\mu_0}{\epsilon_3}}E_3 - i\omega_3\sqrt{\frac{\mu_0}{\epsilon_3}}\,dE_1^2 e^{i(\Delta k)z}$$

where $$-\frac{\sigma_1}{2}\sqrt{\frac{\mu_0}{\epsilon_1}} \text{ and } -\frac{\sigma_3}{2}\sqrt{\frac{\mu_0}{\epsilon_3}}$$

are the loss terms. The above formulas, therefore, represent a mathematical description of the absorption properties of the nonlinear material to the fundamental energy and the newly generated harmonic energy.

An efficient protection device has only to absorb a sufficient amount of the energy to reduce the hostile laser energy to an eye safe level. This results in a greatly lowered concern for phase matching and independent of phase, the MF/MC device exhibits a strong absorption of nonlinear energy within a quite short path. Fortunately, concern with precise orientation of the material also becomes of little concern and enables the use of liquid crystals and nonlinear plastics. It should be understood that one advantage to using ultra small diameter optical fibers is that they conduct light and can be made long enough to absorb the required number of nonlinear energy cycles created by phase mismatching. The intensity of the propagating laser energy is maintained at a high level in ultra small optical fibers and internal reflection creates regions or zones along the optical path where the intensity is sufficiently high for efficient nonlinear absorption to occur.

Figure 6:
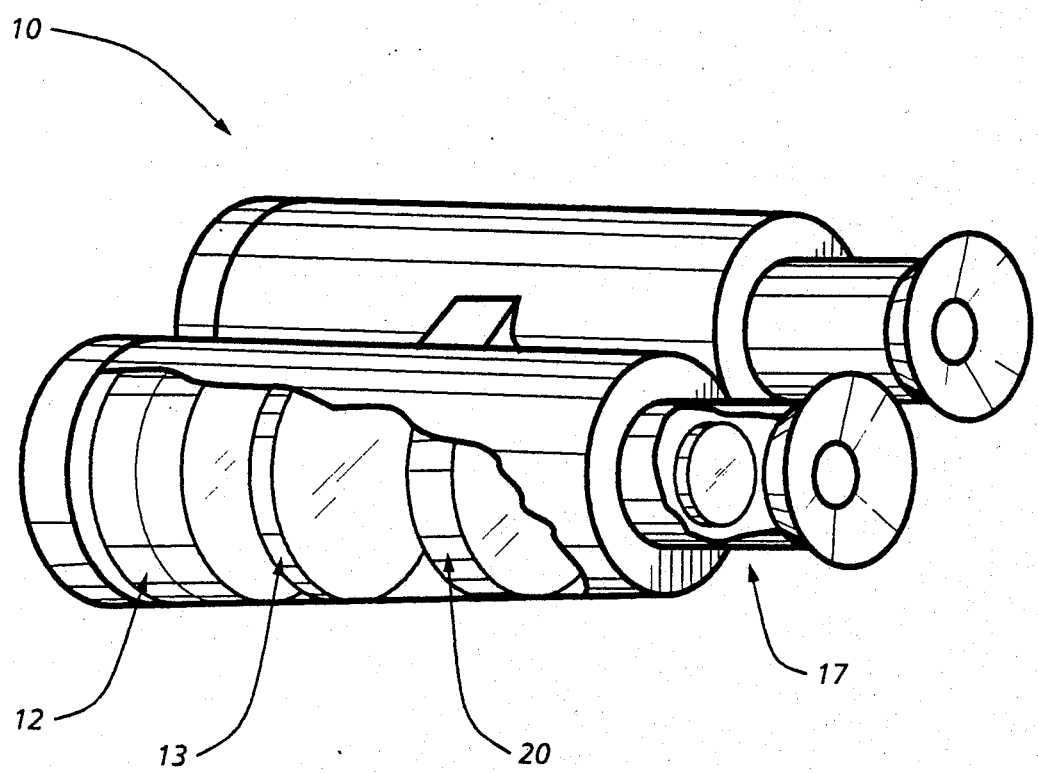
FIG. 6 is a pictorial of a binocular arrangement using a multifiber/multichannel nonlinear array.

FIG. 6 shows a binocular arrangement according to the instant invention. The numbering of FIG. 6 corresponds to the numbering of FIG. 3.

The specification herein discussed is not meant as a limitation on the scope of the method of the invention and its underlying theory as described in connection with the disclosed device. For instance, it is anticipated that devices of many types will be adapted for use in laser machining environments to protect employees and this disclosure is not limited to military applications. Various changes may be made without departing from the scope of the invention as defined in the following claims.

What is claimed as new and desired to be secured by Letters Patent of the United States is:

1. An optical hardening device for eye protection against frequency agile lasers comprising:
   a first and second means for focusing incoming optical energy;
   a first and second bandpass filter in spaced relationship with said means for focusing incoming optical energy, whereby unwanted optical wavelengths are filtered;

a first and second passive, coherent-energy attenuating element comprised of an array of second harmonic nonlinear optic fibers spaced at the focal points of the incoming energy focused by said means for focusing whereby all first elements are in spaced parallel relationship to all second elements, forming binoculars.

2. An optical hardening device for protection against frequency agile lasers comprising:

an array of second harmonic, nonlinear, optical fibers having the properties of generating and absorbing a second harmonic from an input, and a means for focusing incoming optical energy into an image for inputting to said array, and a bandpass filter in spaced relationship between said array and said means for focusing to filter unwanted frequencies.

3. An optical hardening device according to claim 2 wherein said nonlinear optical fibers are organic polymers.

4. An optical hardening device for protection against frequency agile lasers according to claim 2 wherein said bandpass filter filters ultraviolet and infrared radiation from the array thus limiting the output of said array to visible spectrum.

5. An optical hardening device according to claim 2 wherein said array of fibers are formed of liquid crystal.

* * * * *